(12) United States Patent
Maetzler

(10) Patent No.: US 11,733,253 B2
(45) Date of Patent: Aug. 22, 2023

(54) WORKLOAD INSTRUMENT MASKING

(71) Applicant: Roche Diagnostics Operations, Inc., Indianapolis, IN (US)

(72) Inventor: Marco Maetzler, Belmont, CA (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 96 days.

(21) Appl. No.: 17/119,307

(22) Filed: Dec. 11, 2020

(65) Prior Publication Data
US 2021/0190802 A1 Jun. 24, 2021

(30) Foreign Application Priority Data
Dec. 23, 2019 (EP) ..................................... 19383181

(51) Int. Cl.
*G01N 35/00* (2006.01)

(52) U.S. Cl.
CPC ... *G01N 35/0092* (2013.01); *G01N 35/00871* (2013.01)

(58) Field of Classification Search
CPC ......... G01N 35/0092; G01N 35/00871; G16H 40/20
See application file for complete search history.

(56) References Cited

U.S. PATENT DOCUMENTS

2007/0191721 A1* 8/2007 Parker .................. G16H 10/60
600/509
2007/0250344 A1* 10/2007 Stephenson ............ G16H 40/20
705/2
2008/0312893 A1* 12/2008 Denton .................. G16H 50/20
703/11
2015/0276782 A1 10/2015 Riether

FOREIGN PATENT DOCUMENTS

| JP | H11-316236 A | 11/1999 |
|----|----|----|
| JP | 2018-025529 A | 2/2018 |
| WO | 2013/174906 A1 | 11/2013 |
| WO | 2016/075755 A1 | 5/2016 |

OTHER PUBLICATIONS

European Search Report dated Jun. 4, 2020, in Application No. 19383181.5, 2 pp.
Pastor, Rafael et al., Laboratories as a Service (LaaS): Using Cloud Technologies in the Field of Education, Journal of Universal Computer Science, 2013, pp. 2112-2126, vol. 19, No. 14.

* cited by examiner

*Primary Examiner* — Shogo Sasaki
(74) *Attorney, Agent, or Firm* — Roche Diagnostics Operations, Inc.

(57) ABSTRACT

A method to optimize analyzer use in a laboratory having a plurality of analyzers based on laboratory workload is presented. The method comprises determining current laboratory workload, calculating workload capability of the plurality of analyzers minus one analyzer if the current laboratory workload is below a threshold criteria and if there are two or more analyzers in the plurality of analyzers, masking one of the plurality of analyzers if the current workload is met by the plurality of analyzers minus one analyzer, proceeding with current workload, and repeating the above steps until the current laboratory workload has been completed.

17 Claims, 4 Drawing Sheets

WORKLOAD INSTRUMENT MASKING

CROSS-REFERENCE TO RELATED APPLICATIONS

This application claims priority to EP 19383181.5, filed Dec. 23, 2019, which is hereby incorporated by reference.

BACKGROUND

The present disclosure generally relates to the optimization of analyzer workload for a laboratory.

In a typical laboratory set-up, load balancing between two or more analyzers is set to a static ratio such as, for example, a 1:1 or 1:2 tube distribution between the different analyzers in the laboratory. If the laboratory is running a typical average workload, this static distribution between the analyzers is adequate. However, if the laboratory workload falls below average such as, for example, at the point where a single workstation could handle the entire workload by itself, the load distribution between the analyzers becomes wasteful in terms of energy, reagents, and the like due to the fact that two analyzers are being utilized when one analyzer could handle the job. This situation also arises when laboratory workload balancing is applied to a laboratory having more than two analyzers.

Therefore, there is a need to mask certain analyzers when the workload falls below a certain threshold in order to save lab resources.

SUMMARY

According to the present disclosure, a method to optimize analyzer use in a laboratory having a plurality of analyzers based on laboratory workload is disclosed. The method comprises determining current laboratory workload, calculating workload capability of the plurality of analyzers minus one analyzer if the current laboratory workload is below a threshold criteria and if there are two or more analyzers in the plurality of analyzers, masking one of the plurality of analyzers if the current workload is met by the plurality of analyzers minus one analyzer, proceeding with current workload, and repeating the above steps until the current laboratory workload has been completed.

In accordance with one embodiment of the present disclosure, a laboratory system is also disclosed. The laboratory system can comprise a plurality of analyzers, a control device communicatively connected to the plurality of analyzers via a communication network and configured to carry out the above method, and a data management unit communicatively coupled to the control device via a communication network and configured to receive task orders and to send the task orders to the control device.

Accordingly, it is a feature of the embodiments of the present disclosure to mask certain analyzers when the workload falls below a certain threshold in order to save lab resources. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
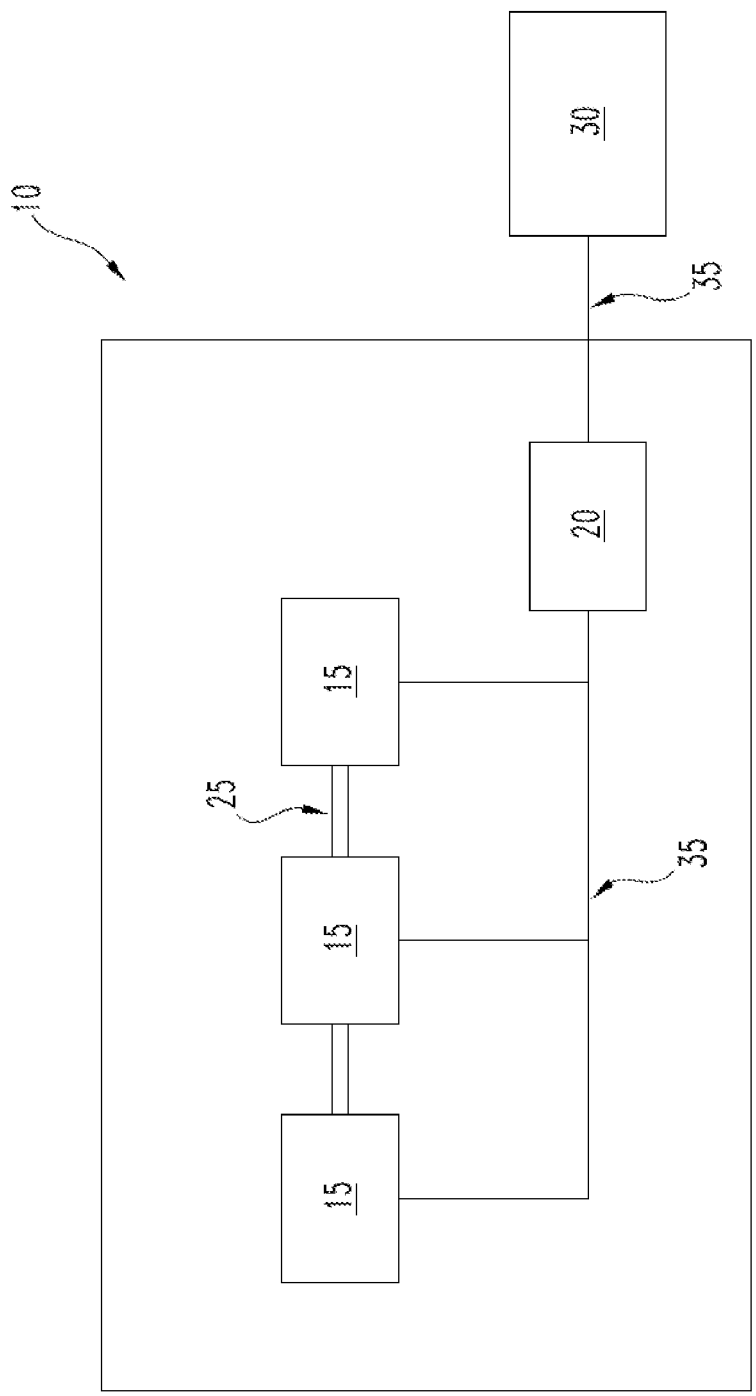
FIG. 1 illustrates a laboratory comprising a plurality of analyzers according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method to optimize analyzer use in a laboratory having a plurality of analyzers based on laboratory workload is presented. The method comprises the steps of determining current laboratory workload, calculating workload capability of the plurality of analyzers minus one analyzer if the current laboratory workload is below a threshold criteria and if there are two or more analyzers in the plurality of analyzers, masking one of the plurality of analyzers if the current workload is met by the plurality of analyzers minus one analyzer, proceeding with current workload, and repeating the above steps until the current laboratory workload has been completed.

The term 'analyzer'/'analytical instrument' as used herein can encompass any apparatus or apparatus component configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent-holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzer are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'workflow' as used herein can refer to a collection of workflow steps/processing steps. According to particular embodiments, the workflow can define a sequence in which the processing steps can be carried out.

The term 'workflow step' as used herein can encompass any activity belonging to a workflow. The activity can be of an elementary or complex nature and can be typically performed at or by one or more work cell(s).

In one embodiment, the method can further comprise unmasking any available masked analyzers if the current workload is not met by the capability of the plurality of analyzers minus one analyzer.

In one embodiment, the steps of the method are repeated until there is only one analyzer being utilized in the plurality of analyzers.

In one embodiment, the method can further comprise the step of communicating the current laboratory workload to the plurality of analyzers via a control device. The control device can be communicatively connected to the plurality of analyzers via a communication network. The control unit can be located within the laboratory or can be located external from the location of the laboratory.

The term 'control device' as used herein can encompass any physical or virtual processing device configurable to control a laboratory instrument or system comprising one or more laboratory instruments in a way that workflow(s) and workflow step(s) can be conducted by the laboratory instrument/system. The control device may, for example, instruct the laboratory instrument/system to conduct pre-analytical, post analytical and analytical workflow(s)/workflow step(s). The control device may receive information from a data management unit regarding which steps need to be performed with a certain sample. In some embodiments, the control device may be integral with a data management unit, may be comprised by a server computer and/or be part of one laboratory analyzer or even distributed across multiple analyzers of the analytical laboratory. The control device may, for instance, be embodied as a programmable logic controller running a computer-readable program provided with instructions to perform operations.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

In one embodiment, the control device is communicatively connected to a data management unit, wherein the data management unit can be a LIS (laboratory information system) and/or HIS (hospital information system). The control device can be communicatively connected to the data management unit via a communication network. The control device can also be communicatively connected to the data management unit via a cloud solution. The data management unit receives task orders to be completed by the laboratory and communicates those task orders to the control unit.

A 'data management unit' or 'database' can be a computing unit for storing and managing data. This may involve data relating to biological sample(s) to be processed by the plurality of analyzers in the laboratory. The data management unit may be connected to an LIS (laboratory information system) and/or an HIS (hospital information system).

The data management unit can be a unit within or co-located with a laboratory instrument with the laboratory. It may be part of the control unit. Alternatively, the database may be a unit remotely located. For instance, it may be embodied in a computer connected via a communication network.

In one embodiment, the current laboratory workload is determined based on received task orders, open test orders, number of samples, and combinations thereof.

A 'test order' as used herein can encompass any data object, computer loadable data structure, modulated data representing such data being indicative of one or more processing steps to be executed on a particular biological sample. For example, a test order may be a file or an entry in a database. A test order can indicate an analytical test if, for example, the test order can comprise or can be stored in association with an identifier of an analytical test to be executed on a particular sample.

In one embodiment, the threshold criteria comprises current workload load of the laboratory, reagent availability in the individual analyzers of the plurality of analyzers, throughput capability of the plurality of analyzers, ability of the individual analyzers in the plurality of analyzers to receive stat samples, next estimated maintenance event of the individual analyzers of the plurality of analyzers, future workload changes, cost per test, and combinations thereof.

A 'STAT sample' can be a sample which needs to be processed and analyzed very quickly by the analyzer as the analysis result of that sample may be of life-crucial importance for a patient.

In one embodiment, one of the analyzers in the plurality of analyzers can be masked if it is determined that the reagent availability at that analyzer is too low to process samples for the current laboratory workload.

In one embodiment, one of the analyzers in the plurality of analyzers can be masked if it is determined that the next estimated maintenance event at that particular analyzer falls within a certain time period.

In one embodiment, the certain time period is calculated to occur during the processing of the current laboratory workload.

In one embodiment, the plurality of analyzers in the laboratory comprise similar type analyzers that are capable of performing similar types of sample analysis.

In one embodiment, the plurality of analyzers in the laboratory are connected to each other via a transport system.

The term 'transport system' as used herein can encompass any apparatus or apparatus component that can be configured to transport sample carriers (each holding one or more sample containers) between laboratory analyzers. In particular, the transport system can be a one dimensional conveyor-belt based system, a two-dimensional transportation system (such as a magnetic sample carrier transport system) or a combination thereof.

A laboratory system is also presented. The laboratory system comprises a plurality of analyzers, a control device communicatively connected to the plurality of analyzers and configured to carry out the above method, and a data management unit communicatively coupled to the control device.

In one embodiment, the laboratory system further comprises a transport system configured to transport samples between the plurality of analyzers.

Referring initially to FIG. 1, FIG. 1 illustrates a laboratory 10 comprising a plurality of analyzers 15. The plurality of analyzers 15 can be similar in that they generally capable of performing the same types of tests on samples. The plurality of analyzers 15 can be connected to each other by a transport system 25 such as, for example, a conveyor belt or a magnetic sample carrier transport system, in order to transport samples between the different analyzers in the plurality of analyzers 15.

Further, the plurality of analyzers 15 is communicatively connected to a control device 20 via a communication network 35. The control device 20 is shown to be located within the laboratory 10 in FIG. 1. However, the control unit 20 can be located outside the laboratory 10. In turn, the control device 20 is communicatively connected to a data management unit 30 via a communication network 35. The data management unit 30 may be located within the laboratory 10 or may be at a remote location. In one embodiment, the data management unit 30 may be connected to a cloud system (not shown) and the control device 20 may also be connected to the cloud system.

Task orders are received by the data management unit 30 and are communicated to the control unit 30. In one embodiment, the control unit 20 then determines the current workload need of the laboratory based on these received task orders among other things.

Figure 2:
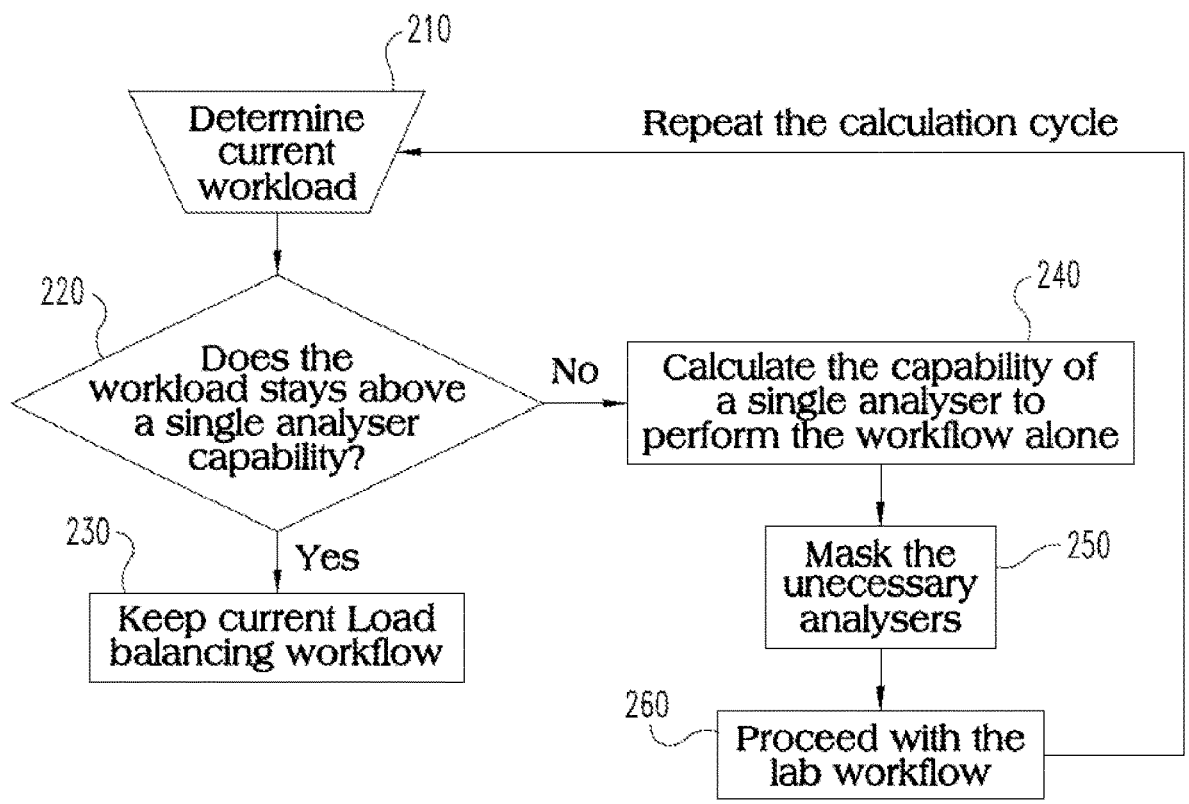
FIG. 2 illustrates a flowchart illustrating the optimization of a laboratory comprising two analyzers according to an embodiment of the present disclosure.

FIG. 2 is a flowchart illustrating the method of the optimization of a laboratory comprising only of two analyzers. Starting with step 210, the current workload of the laboratory is determined. The current laboratory workload can include anything associated with the utilization of the analyzers in the laboratory 10 such as, for example, task orders, open orders, sample numbers, and the like. This determined current laboratory workload is then compared to the workload capability of one analyzer, in step 220. The workload capability of an analyzer is typical workload the analyzer is capable of handling for a set period of time. If the current laboratory workload is above the workload capability of a single analyzer, the current laboratory workload balancing workflow is maintained in step 230.

However, if the current laboratory workload is below the workload capability of a single analyzer, then the workload capability of the two analyzers is calculated in step 240. If it is determined that one of the two analyzers could perform the current laboratory workload on its own, then the other analyzer is masked, i.e., turned off, in step 250 and the laboratory proceeds with processing the laboratory workflow in step 260.

This method is repeated throughout the processing of the laboratory workflow. If, however, there comes a time that is determined in step 220 that the single analyzer can no longer meet the demand of the current laboratory workload, the other analyzer can be unmask, i.e., turn on, and return to service to meet the demand of the current laboratory workload. The method again is repeated until the processing of the laboratory workflow is completed.

Figure 3:
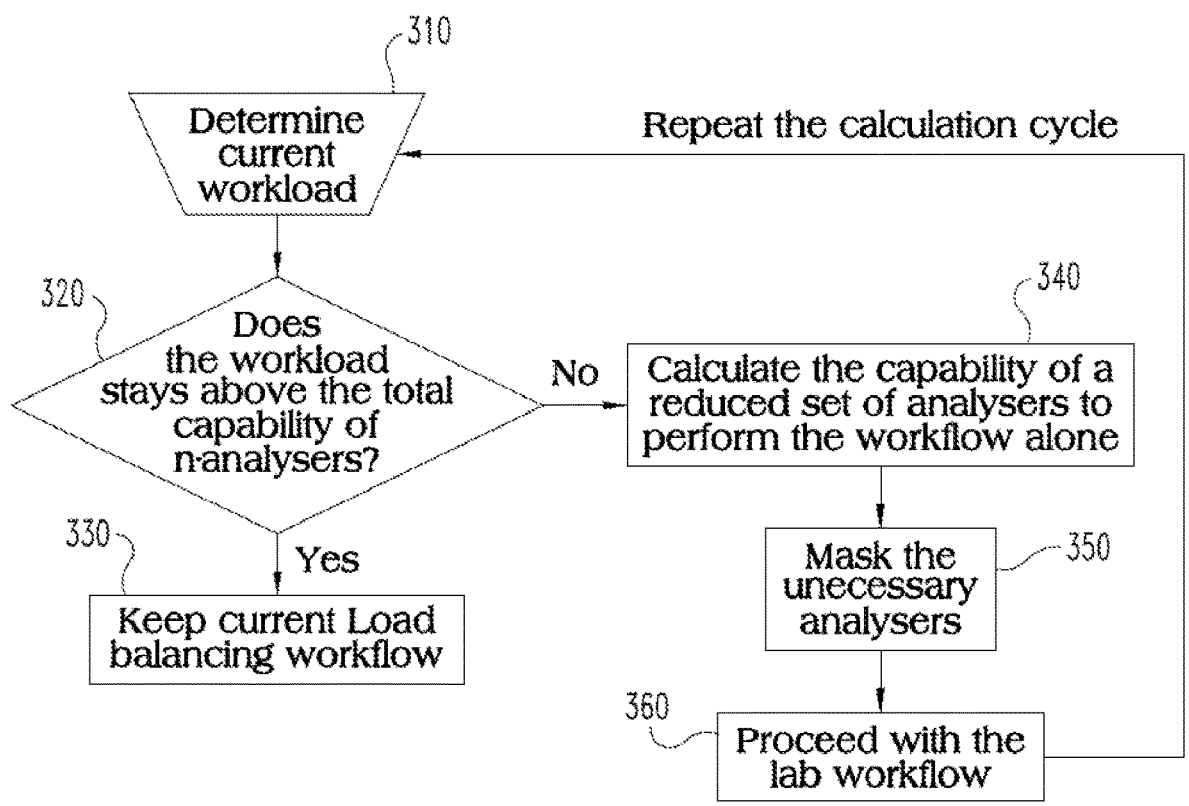
FIG. 3 illustrates a flowchart illustrating the optimization of a laboratory comprising a plurality of analyzers according to an embodiment of the present disclosure.

FIG. 3 is a flowchart illustrating the method of the optimization of a laboratory comprising a plurality of analyzers. Starting with step 310, as with the flowchart illustrated in FIG. 2, the current workload of the laboratory is determined.

The current laboratory workload is then compared against a threshold criteria, in step 320. In one embodiment, the threshold criteria can be the total workload capability of the plurality of analyzers. In other embodiments, the threshold criteria can include not only the total workload capability of the plurality of analyzers but also the reagent availability in the analyzers, throughput capability of the analyzers, the analyzer's ability to receive STAT samples, next estimated maintenance event for the analyzers, future workload changes, cost per test, and the like. If the current laboratory workload is above the threshold criteria, the current laboratory workload balancing workflow is maintained in step 330.

However, if the current laboratory workload is below the threshold criteria, then the workload capability of a reduced number of analyzers is calculated, in step 340, to determine if a reduced number of analyzers can perform the current laboratory workload. If it is determined that the reduced number of analyzers can perform the current laboratory workload and there is more than one analyzer performing the current laboratory workload, then the one or more analyzer is masked, i.e., turned off, in step 350, and the laboratory proceeds with processing the laboratory workflow in step 360.

This method is repeated throughout the processing of the laboratory workflow. If, however, there comes a time that is determined in step 320 that the reduced number of analyzers can no longer meet the demand of the current laboratory workload, a masked analyzer can be unmask, i.e., turn on, and return to service to meet the demand of the current laboratory workload. The method again is repeated until the processing of the laboratory workflow is completed.

In other embodiments as mentioned above, the analyzer selection criteria may not only considerate the laboratory workload capability but can also take into account other laboratory aspects that could affect the analyzer's ability to process samples and/or tasks. For example, the amount of reagent currently available in the analyzer can affect the ability of the analyzer to process samples or perform analysis on those samples. For example, if the reagent level of the analyzer is too low to perform an analysis on samples, the control device 20 can mask that analyzer until the reagent level is brought up to the acceptable level that is capable of performing analysis on samples again.

In other embodiment, the control device 20 can take into consideration the throughput capability of the analyzer when deciding whether to mask or unmask a certain analyzer in the laboratory 10. For example, if one analyzer has a lower throughput capability than other analyzers in the plurality of analyzers 15 in the laboratory 10, the control device 20 may decide to mask the analyzer with the lower throughput before other analyzers in the plurality of analyzers 15 if the analyzers with the higher throughput capability are capable of handling the laboratory workload.

In another embodiment, the control device 20 can take into consideration the ability of the different analyzers in the plurality of analyzers 15 to receive STAT samples. For example, if only one analyzer in the plurality of analyzers 15 in the laboratory 10 has the capability to receive and process STAT samples and the laboratory 10 is known to receive STAT samples, it would not make sense to mask that analyzer that has the capability to receive and process STAT samples.

In another embodiment, the control device 20 can take into consideration the next estimated maintenance event for the different analyzers in the plurality of analyzers 15 in the laboratory 10. For example, an analyzer can be masked if the next estimated maintenance event at that analyzer falls within a certain time period. For example, if that certain time period is determined to occur during the processing of the current laboratory workload, that particular analyzer can be masked until the maintenance is performed on the analyzer. Once the maintenance has been completed, that analyzer can be unmasked.

In another embodiment, the control device 20 can take into consideration a total workload estimation, i.e., future predicted workload changes, of the laboratory 10 when deciding which analyzers in the plurality of analyzers 15 in the laboratory 10 to mask or unmask. For example, if it is known that first thing in the morning, i.e., the start of the typical work day, the laboratory workload is quite high, the control device 20 may unmask all the analyzers in the plurality of analyzers 10. In contrast, if it is known that the laboratory workload tends to taper off in the late evening hours, the control device 20 may plan to mask some of the analyzers in the plurality of analyzers 15 during this time period.

In another embodiment, the control device 20 can take into consideration the cost per test to run the different test orders on the different analyzers in the plurality of analyzers 15 when deciding whether to mask or unmask certain analyzers in the laboratory 10.

As can be seen, the control device 20 can constantly adapt the number of available analyzers in the plurality of analyzers 15 in the laboratory 10 based on the current laboratory workload. If the laboratory workload grows, the control device 20 has the ability to unmask analyzers in order for the unmasked analyzers to help with the laboratory workload. If the laboratory workload lessens, the control device 20 has the ability to mask analyzers in the plurality of analyzers 15 one by one in order to optimize the analyzer workload in the laboratory 10. By using only the number of analyzers needed to complete the laboratory workload, the laboratory 10 will become more efficient and will save energy, reagents, wear and tear on the analyzers, and the like.

The laboratory system will, therefore, become a self-regulating system. In order words, the output, that is, the workload of the plurality of analyzers 15, can be controlled as a function of the input, that is, the laboratory workload, wherein the laboratory workload can comprise task orders, open tests yet to be done, number of samples to be processed, and the like.

Figure 4:
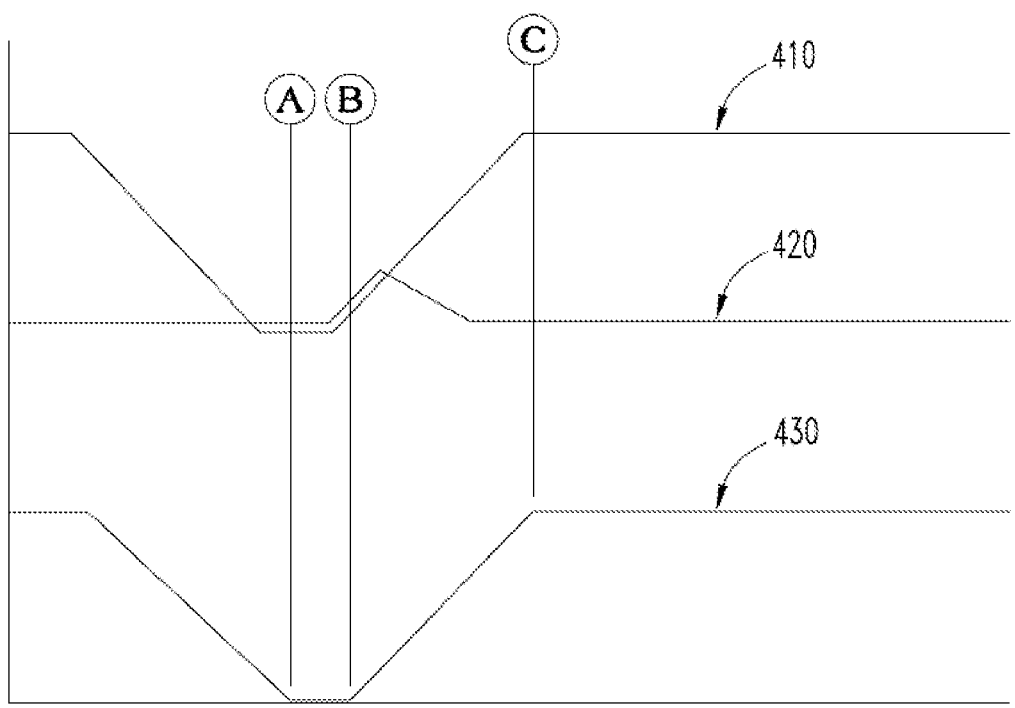
FIG. 4 illustrates a graph illustrating the calculation cycle for laboratory optimization according to an embodiment of the present disclosure.

FIG. 4 illustrates a graph showing the calculation cycle for laboratory optimization. In the graph, line 410 represents the workload of the entire laboratory over a period of time. Line 420 represents the workload of a first analyzer in the laboratory and line 430 represents the workload of a second analyzer in the laboratory.

As the workload of the laboratory lessens, the amount of workload conducted by the second analyzer also falls until the point where the first analyzer is capable of handling the entire laboratory workload by itself. At that point, point A in FIG. 4, the second analyzer is masked, i.e., the second analyzer no longer accepts samples to analyze or, in other words, is turned off, and the first analyzer handles the entire laboratory workload.

Eventually, the workload of the laboratory increases to point where the first analyzer no longer has the capability of handling the whole laboratory workload by itself. At that point, point B in FIG. 4, the second analyzer is unmasked, i.e., the second analyzer begins to accept samples to analyze again or, in other words, is turned on.

As the second analyzer ramps up its capability to analyze samples, the first analyzer ramps down its capability to analyze samples until both analyzers reach a steady state of work, point C in FIG. 4. The laboratory workload and the workloads of the individual analyzers are constantly monitored by a control unit in order to adjust the number of analyzers needed to complete the laboratory workload in the most efficient manner.

It should be noted that even though only two analyzers are represented in the graph in FIG. 4, the calculation of masking/unmasking analyzers in accordance to the laboratory workload can be applied to situations of more than two analyzers in a laboratory.

Further disclosed and proposed is a computer program product including computer-executable instructions for performing the disclosed method in one or more of the embodiments enclosed herein when the program is executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

As used herein, a computer program product can refer to the program as a tradable product. The product may generally exist in any format, such as in a downloadable file, on a computer-readable data carrier on premise or located at a remote location (cloud). Specifically, the computer program product may be distributed over a data network (such as a cloud environment). Furthermore, not only the computer program product, but also the execution hardware may be located on-premise or in a cloud environment.

Further disclosed and proposed can be a computer-readable medium comprising instructions which, when executed by a computer system, can cause an analytical laboratory to perform the method according to one or more of the embodiments disclosed herein.

Further disclosed and proposed can be a modulated data signal comprising instructions which, when executed by a computer system, can cause an analytical laboratory to perform the method according to one or more of the embodiments disclosed herein.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A computer implemented method to optimize analyzer use in a laboratory having a plurality of analyzers based on laboratory workload, the method comprising:
   a) determining a current laboratory workload wherein a laboratory workload is based on a level of operation required by the plurality of analyzers to complete laboratory tests on biological samples designated for processing, and determining a current workload capability of the plurality of analyzers, wherein the current workload capability is based on a determined ability of the plurality of analyzers to complete laboratory tests;
   b) in response to determining that the current laboratory workload is below a first predetermined level or that the workload capability of the plurality of analyzers exceeds a second predetermined level, calculating an adjusted workload capability of the plurality of analyzers that are not masked minus one analyzer, wherein masking an analyzer omits or causes removing use of the analyzer from processing the current laboratory workload;

c) in response to determining that the current workload is met by the adjusted workload capability of the plurality of analyzers, masking one of the unmasked analyzers of the plurality of analyzers;

d) causing a processing of the current laboratory workload utilizing the unmasked analyzers of the plurality of analyzers; and e) repeating steps a) through d) until the current laboratory workload has been completed.

2. The method according to claim 1, further comprising, in response to determining that the current workload is not met by the adjusted workload capability of the plurality of analyzers, unmasking any masked analyzers of the plurality of analyzers.

3. The method according to claim 1, wherein step e) is repeated until there is only one analyzer.

4. The method according to claim 1, further comprising, communicating the current laboratory workload to the plurality of analyzers via a control device, wherein the control device is connected to a data management unit.

5. The method according to claim 4, wherein the data management unit is a LIS and/or HIS.

6. The method according to claim 4, wherein the data management unit receives task orders to be completed and communicates those task orders to the control unit.

7. The method according to claim 1, wherein the current laboratory workload is determined based on received task orders, open orders, number of samples, and combinations thereof.

8. The method according to claim 1, wherein the threshold criteria comprises current workload load, reagent availability, throughput capability, ability to receive stat samples, next estimated maintenance event, future workload changes, cost per test, and combinations thereof.

9. The method of claim 8, wherein an analyzer in the plurality of analyzers is masked if the reagent availability at that analyzer is too low to perform analysis on samples in the current laboratory workload.

10. The method of claim 8, wherein an analyzer in the plurality of analyzers is masked if the next estimated maintenance event at that analyzer falls within a certain time period.

11. The method of claim 10, wherein the certain time period is calculated to occur during the processing of the current laboratory workload.

12. The method according to claim 1, wherein the plurality of analyzers comprise similar type analyzers that perform at least some of the same type of sample analysis.

13. The method according to claim 1, wherein the plurality of analyzers are connected to each other via a transport system.

14. The method of claim 1 wherein the determined ability of the plurality of analyzers to complete laboratory tests is based on calculating a typical throughput of an analyzer of the plurality of analyzers.

15. The method of claim 1 wherein the determined ability of the plurality of analyzers to complete laboratory tests is based on determining a level of reagent installed within or available from the laboratory to the plurality of analyzers.

16. A laboratory system, the laboratory system comprising:
a plurality of analyzers;
a control device communicatively connected to the plurality of analyzers via a communication network and configured to carry out the method of claim 1; and
a data management unit communicatively coupled to the control device via a communication network and configured to receive task orders and to send the task orders to the control device.

17. The laboratory system according to claim 16, further comprising,
a transport system configured to transport samples between the plurality of analyzers.

* * * * *